(12) United States Patent
Hwang et al.

(10) Patent No.: US 9,089,842 B2
(45) Date of Patent: Jul. 28, 2015

(54) MULTI-MODAL SURFACE PLASMON POLARITON—RAMAN SCATTERING BASED BIO-DETECTION

(75) Inventors: Grace M. Hwang, Bedford, MA (US); Lin Pang, La Jolla, CA (US); Yeshaiahu Fainman, La Jolla, CA (US)

(73) Assignee: The MITRE Corporation, McLean, VA (US)

( * ) Notice: Subject to any disclaimer, the term of this patent is extended or adjusted under 35 U.S.C. 154(b) by 605 days.

(21) Appl. No.: 12/770,411

(22) Filed: Apr. 29, 2010

(65) Prior Publication Data

US 2010/0208253 A1 Aug. 19, 2010

Related U.S. Application Data

(62) Division of application No. 12/073,994, filed on Mar. 12, 2008, now abandoned.

(51) Int. Cl.
| | |
|---|---|
| *G01N 21/01* | (2006.01) |
| *B01L 3/00* | (2006.01) |
| *G01N 21/552* | (2014.01) |
| *G01N 21/65* | (2006.01) |
| *G01N 21/03* | (2006.01) |

(52) U.S. Cl.
CPC ........ *B01L 3/502715* (2013.01); *G01N 21/554* (2013.01); *G01N 21/65* (2013.01); *G01N 21/658* (2013.01); *G01N 2021/0346* (2013.01)

(58) Field of Classification Search
None
See application file for complete search history.

(56) References Cited

U.S. PATENT DOCUMENTS

| | | | |
|---|---|---|---|
| 6,064,897 A | 5/2000 | Lindberg et al. | |
| 7,148,031 B2 | 12/2006 | Mullen | |
| 7,171,312 B2 | 1/2007 | Steinthal et al. | |
| 7,271,914 B2 | 9/2007 | Lin et al. | |
| 8,094,314 B2 | 1/2012 | Tetz et al. | |
| 2001/0053521 A1* | 12/2001 | Kreimer et al. | 435/6 |
| 2003/0073139 A1 | 4/2003 | Kreimer et al. | |
| 2003/0227628 A1* | 12/2003 | Kreimer et al. | 356/419 |
| 2006/0110818 A1 | 5/2006 | Hill et al. | |
| 2007/0030481 A1 | 2/2007 | Gilbert | |
| 2009/0233810 A1 | 9/2009 | Hwang et al. | |

OTHER PUBLICATIONS

Lyon et al (1998 Anal Chem 70:5177-5183).*
Johnston et al (1997 Anal Chem 69:1844-1851).*
Campbell et al (2007 Biomaterials 28:2380-2292).*
Nagase et al (2012 Analyst 137:5034-5040).*
Hwang et al (2008 IEEE Sensors Journal 8:2074-2079).*
Genet et al (2007 Nature 445:39-46).*
Njoku, Eni G. et al., "Observations of Soil Moisture Using a Passive and Active Low-Frequency Microwave Airborne Sensor During SGP99," IEEE Transactions on Geoscience and Remote Sensing, vol. 40, No. 12, Dec. 2002, pp. 2659-2673.
Pang, Lin et al., "Observation of the Splitting of Degenerate Surface Plasmon Polariton Modes in a Two-Dimensional Metallic Nanohole Array," Applied Physics Letters 90, 111103, 2007, pp. 1-3.
Pang, Lin et al., "Spectral Sensitivity of Two-Dimensional Nanohole Array Surface Plasmon Polariton Resonance Sensor," Applied Physics Letters 91, 123112, 2007, pp. 1-3.
Johnston, K. S., and Yee, S. D., "Calibration of Surface Plasmon Resonance Refractometers Using Locally Weighted Parametric Regression," in *Analytical Chemistry*, vol. 69, No, 10, 1844-1851, American Chemical Society (May 15, 1997).
Kocabas, A., et al., "Excitation of a surface plasmon with an elastomeric grating," in *Applied Physics Letters*, vol. 89, 041123-1-041123-3, American Institute of Physics (Jul. 26, 2006).
Tetz, K. A., et al., "High-resolution surface plasmon resonance sensor based on linewidth-optimized nanohole array transmittance," in *Optics Letters*, vol. 31, No. 10, 1528-1530, Optical Society of America (May 15, 2006).

* cited by examiner

*Primary Examiner* — Christopher M Gross
(74) *Attorney, Agent, or Firm* — Sterne, Kessler, Goldstein & Fox P.L.L.C.

(57) ABSTRACT

Methods and systems for combined SPP and Raman scattering-based bio-detection are provided. Embodiments include a bio-detection system having a microfluidics chip, a Surface Plasmon Polariton (SPP)-based system component, and a Raman scattering-based system component. The SPP-based and the Raman scattering-based system components can be used simultaneously or individually separately to detect biological and/or chemical analytes. The bio-detection system further includes an aerosol collector chip. Embodiments of the present invention can be used aboard means of propagation of biological and/or chemical analytes, including, for example, commercial aircrafts. Embodiments of the present invention can be used to enable an aircraft warning system.

19 Claims, 10 Drawing Sheets

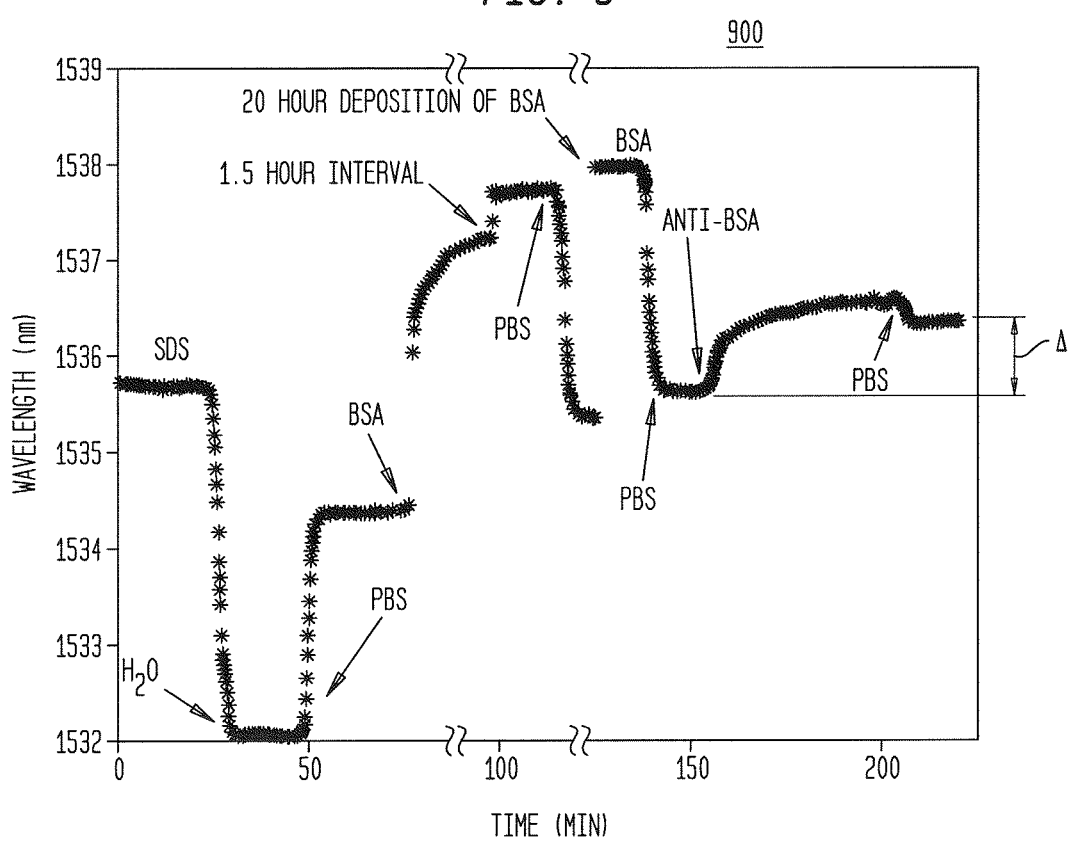

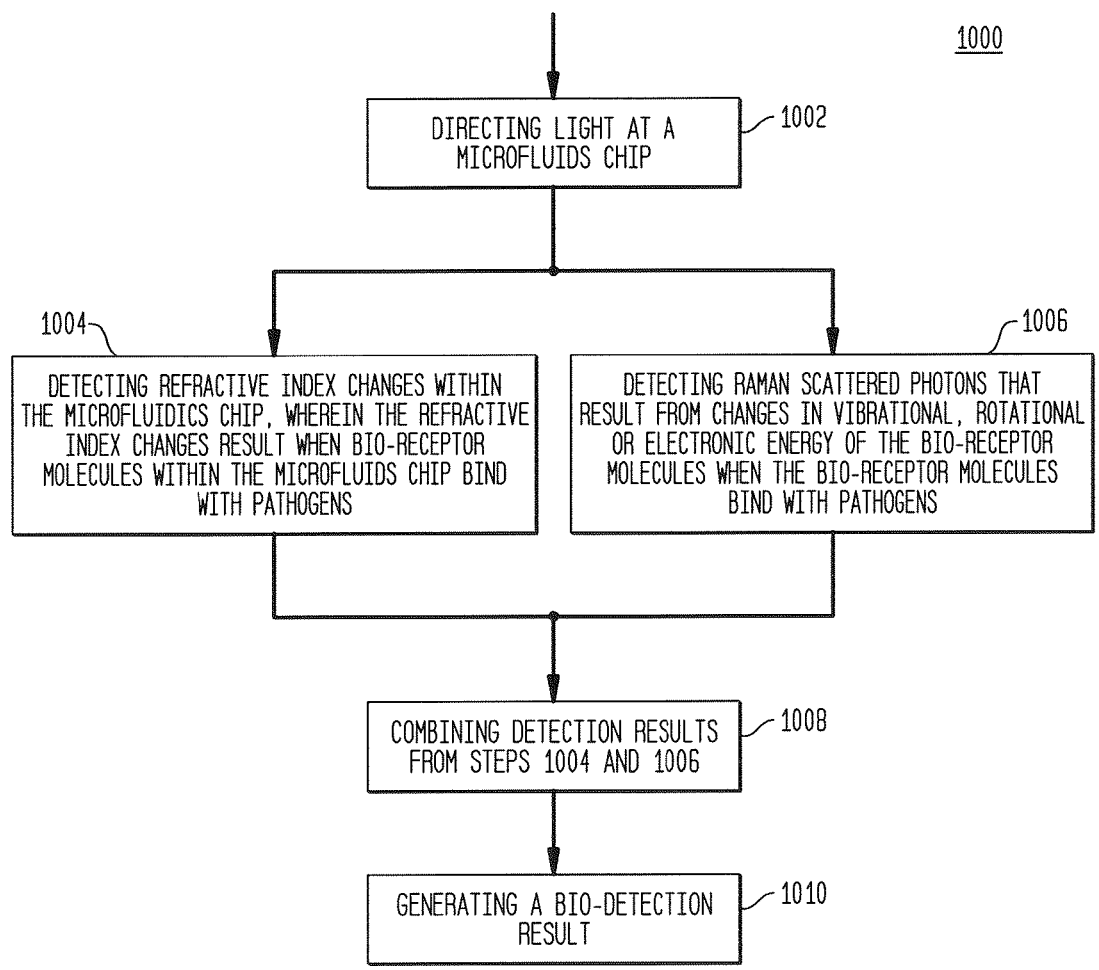

MULTI-MODAL SURFACE PLASMON POLARITON—RAMAN SCATTERING BASED BIO-DETECTION

CROSS-REFERENCE TO RELATED APPLICATIONS

This application is a Divisional Application of (now abandoned) U.S. patent application Ser. No. 12/073,994, filed Mar. 12, 2008, which is incorporated herein by reference in its entirety.

BACKGROUND OF THE INVENTION

1. Field of the Invention

The present invention relates generally to bio-detection, and more particularly to multi-modal bio-detection of biological and/or chemical analytes.

2. Background Art

Bio-sensing systems that can rapidly detect and identify airborne and/or waterborne biological and/or chemical analytes are of particular importance today. These systems can be especially useful to limit the effects of potential epidemic outbreaks, intentional biological warfare attacks, food contamination outbreaks, or waterborne outbreaks (e.g., E. Coli).

Today, bio-sensing systems with acceptable false alarm rates in-situ present enormous challenges. Current bio-detectors fail to meet one or more performance criteria required for high volume applications such as commercial air traffic. These performance criteria include, for example, low false alarm probability ($P_{FA} < 10^{-4}$ per sensor or $P_{FA} < 10^{-6}$ per biosensor system per flight), high-sensitivity detection (probability of detection $P_D > 0.9$), rapid response times (on the order of minutes or less), and limited use of liquid consumable reagents. Furthermore, current bio-detectors are constrained in their ability to measure samples from multiple media, such as their ability to measure particles directly from exhaled breath, in air, water, soil, and on surfaces. In addition, current bio-detectors lack the high energy efficiency and compactness, which are desirable in various situations.

There is a need therefore for bio-sensing methods and systems that meet at least the above described performance criteria. In addition, bio-sensing methods and systems that allow multi-element, highly parallel multi-media sensing, high energy efficiency, and/or compact designs are needed.

BRIEF SUMMARY OF THE INVENTION

Methods and systems for combined SPP-based and Raman scattering-based detection of biological and/or chemical analytes (e.g., infectious viral particles, biowarfare agents, biological and/or chemical analytes, etc.) are provided herein.

Embodiments of the present invention include a microfluidics chip having an elastomer layer with fluidic channels constructed therein and a grating coupler coupled to the elastomer layer. In an embodiment, the grating coupler includes a glass substrate coated with a gold layer. In an embodiment, the gold layer is etched to form a gold nanohole array. The gold layer is coated with bio-receptor molecules, which bind with biological and/or chemical analytes when present in a fluid passed through the fluidic channels of the elastomer layer. In an embodiment, the microfluidics chip includes a gold-liquid interface (where the fluidic channels adjoin the gold layer) and a glass-gold interface (where the glass substrate adjoins the gold layer).

According to embodiments of the present invention, the grating coupling used within the microfluidics chip allows high-intensity, narrow-featured SPP modes to be achieved. Furthermore, the grating coupling allows for the generation of one or more SPP modes. In an embodiment, a first SPP mode is generated at the gold-liquid interface of the microfluidics chip and a second SPP mode is generated at the gold-glass interface of the microfluidics chip. The "second" SPP mode is invariant to the binding of the bio-receptor molecules with biological and/or chemical analytes, and can thus be used to reduce any detection errors due to variations in temperature, pressure, and/or flow. In further embodiments, more than one SPP modes (e.g., lower order SPP modes, higher-order SPP modes) can be generated at the gold-liquid interface as well as at the gold-glass interface.

Embodiments of the present invention further include a bio-detection system that includes the microfluidics chip; a Surface Plasmon Polariton (SPP)-based system that detects local refractive index changes within the microfluidics chip, which result from binding of the bio-receptor molecules with biological and/or chemical analytes; and a Raman scattering-based system that detects Raman-scattered photons, which also result from the binding of the bio-receptor molecules with the biological and/or chemical analytes. The bio-detection system further includes an aerosol collector chip, which collects and concentrates aerosols into fluid, which is passed through the fluidic channels of the microfluidics chip. The aerosol collector chip collects aerosols from exhaled breath, air, water, and/or soil.

According to embodiments of the present invention, the SPP-based system and the Raman scattering-based system can be used simultaneously or individually separately to detect biological and/or chemical analytes. When used simultaneously, the reliability of bio-detection can be improved.

Embodiments of the present invention enable bio-threat detection systems capable of rapid detection and identification of airborne and/or waterborne biological and/or chemical analytes. Bio-threat detection systems according to the present invention can be particularly useful in places where pathogenic agents can spread through exposed populations at high rates, including, for example, hospitals, airports, and rail stations. Further, embodiments of the present invention can be used aboard means of propagation of biological and/or chemical analytes, including, for example, commercial aircrafts. Embodiments of the present invention can be used to enable an aircraft warning system.

Embodiments according to the present invention enable multi-element, highly parallel multi-media sensing (e.g., exhaled breath, air, water, soil), high energy efficiency, and compact designs.

Embodiments according to the present invention are suitable for highly parallel, multi-element analysis, in which a single fluidics channel etched in the elastomer layer includes an array of sample wells (e.g., 100×100 array of sample wells.

Further embodiments, features, and advantages of the present invention, as well as the structure and operation of the various embodiments of the present invention, are described in detail below with reference to the accompanying drawings.

BRIEF DESCRIPTION OF THE DRAWINGS/FIGURES

The accompanying drawings, which are incorporated herein and form a part of the specification, illustrate the present invention and, together with the description, further serve to explain the principles of the invention and to enable a person skilled in the pertinent art to make and use the invention.

FIGS. 6-9 illustrate example experimental results generated using an embodiment of the present invention.

FIG. 10 is process flowchart of a method for bio-detection according to an embodiment of the present invention.

The present invention will be described with reference to the accompanying drawings. Generally, the drawing in which an element first appears is typically indicated by the leftmost digit(s) in the corresponding reference number.

DETAILED DESCRIPTION OF EMBODIMENT(S)

Introduction

Figure 1:
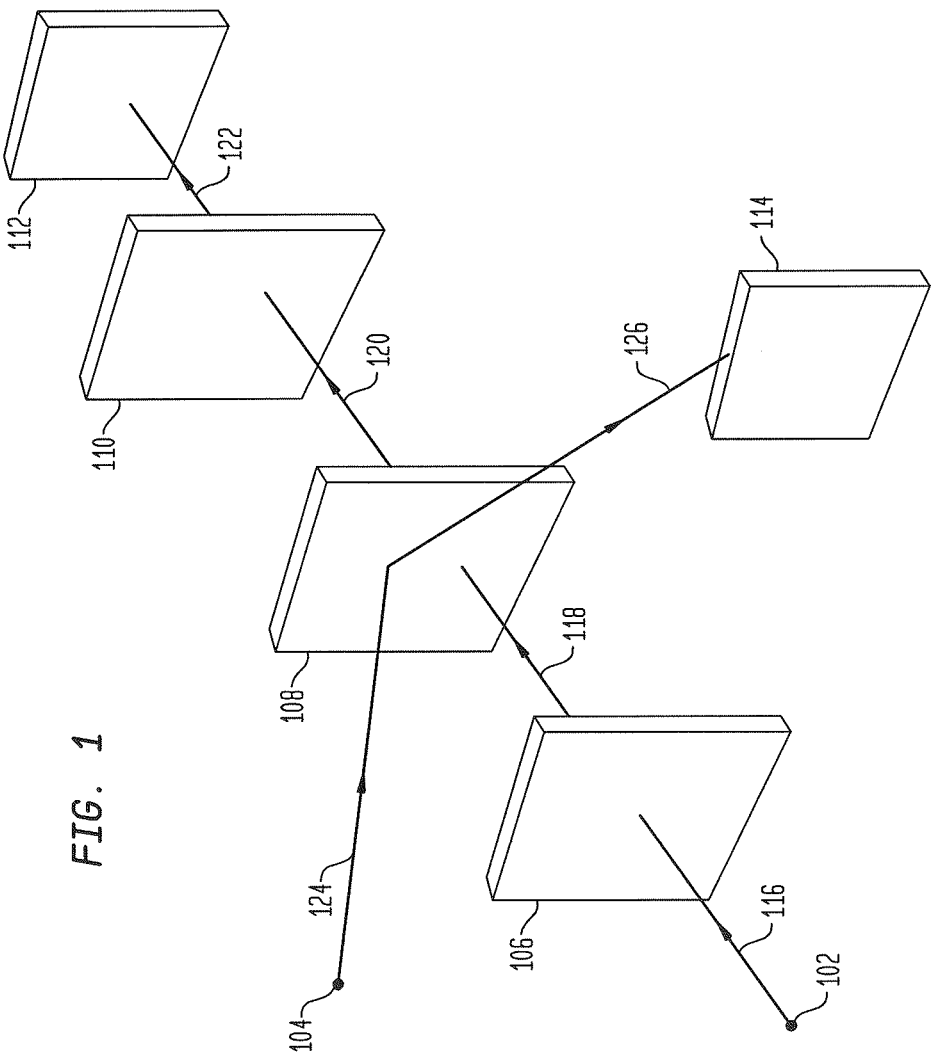
FIG. 1 illustrates an example combined SPP-based and Raman scattering-based bio-detection system.

Bio-sensing systems that can rapidly detect and identify airborne and/or waterborne biological and/or chemical analytes are of particular importance today. These systems can be especially useful to limit the effects of potential epidemic outbreaks, intentional biological warfare attacks, food contamination outbreaks, or waterborne outbreaks (e.g., *E. Coli*).

Today, bio-sensing systems with acceptable false alarm rates in-situ present enormous challenges. Current bio-detectors fail to meet one or more performance criteria required for a viable system. These performance criteria include, for example, low false alarm probability ($P_{FA}<10^{-4}$), high-sensitivity detection (probability of detection $P_D>0.9$), rapid response times (one the order of minutes or less), and limited use of liquid consumable reagents. Furthermore, current bio-detectors are constrained in their ability to measure samples from multiple media, such as air, water, and soil. In addition, current bio-detectors lack the high energy efficiency and compactness, which are desirable in various situations.

One conventional bio-sensing approach is a surface plasmon polariton resonance technique, commonly known as surface plasmon resonance (SPR). A surface plasmon polariton (SPP) is a quasi-electromagnetic wave, generated by p-polarized optical energy, that propagates along the boundary between a dielectric and a metal and is reported to behave like a quasi-free electron plasma. SPR is an optical technique that employs the Kretschmann-Raether geometry, which is widely used in lab-grade bench-top commercial instruments.

The Kretschmann-Raether geometry consists of a prism with one side that is coated by a thin layer of gold (~50 nm) to which receptor molecules, such as antibodies, adhere. The prism is illuminated at an oblique angle through one of the uncoated sides of the prism. Subsequently, reflected photons are monitored by a photo detector collecting photons emitted from the other uncoated side of the prism. Typically, a fluidic channel abuts the thin gold layer where receptor molecules for target analytes are anchored. When the analytes are introduced into the fluidic channel, binding interactions between target analytes and the fixed layer of receptors generate perturbations that result in refractive index changes. The magnitude of these changes is revealed by the dependence of reflection intensity on the wavelength and angle of incidence. Resonant angles, yielding minimum reflection intensities, may also be used to assess the magnitude of refractive index changes.

SPR techniques are today experiencing a reemergence, largely due to advances in nanofabrication that have made it possible to excite and detect surface plasmons with relatively inexpensive and commercially-available instruments. A major drawback of conventional SPR designs, however, remains in the difficulty of incorporating the sensor elements in compact high numerical aperture (NA) imaging systems. This drawback makes conventional SPR designs unsuitable for the type of rapid bio-sensing systems envisioned.

The discovery of enhanced photon transmission through optically dense metal film consisting of periodic sub-wavelength structures has led to recent experimental observation of novel SPP modes. These experiments have been shown to enhance the momentum of an incident beam, obviating the need for a prism, as used by the Kretschmann-Raether setup.

Overview

Methods and systems for combined SPP-based and Raman scattering-based detection of biochemical analytes (e.g., infectious viral particles, biowarfare agents, etc.) or biological and/or chemical analytes are provided herein.

Embodiments of the present invention include a microfluidics chip having an elastomer layer with fluidic channels constructed therein and a grating coupler coupled to the elastomer layer. In an embodiment, the grating coupler includes a glass substrate coated with a gold layer. The gold layer is etched to form a gold nanohole array and is coated with bio-receptor molecules, which bind with biological and/or chemical analytes when present in fluid passed through the fluidic channels of the elastomer layer. In an embodiment, the microfluidics chip includes a gold-liquid interface (where the fluidic channels adjoin the gold layer) and a glass-gold interface (where the glass substrate adjoins the gold layer).

According to embodiments of the present invention, the grating coupling used within the microfluidics chip allows high-intensity, narrow-featured SPP modes to be achieved. Furthermore, the grating coupling allows for the generation of one or more SPP modes. In an embodiment, a first SPP mode is generated at the gold-liquid interface of the microfluidics chip and a second SPP mode is generated at the gold-glass interface of the microfluidics chip. The second SPP mode is invariant to the binding of the bio-receptor molecules with biological and/or chemical analytes, and can thus be used to reduce any detection errors due to variations in temperature, pressure, and/or flow.

Embodiments of the present invention further include a bio-detection system that includes the microfluidics chip; a Surface Plasmon Polariton (SPP)-based system that detects local refractive index changes within the microfluidics chip, which result from binding of the bio-receptor molecules with biological and/or chemical analytes; and a Raman scattering-based system that detects Raman-scattered photons, which also result from the binding of the bio-receptor molecules with the biological and/or chemical analytes. The bio-detection system further includes an aerosol collector chip, which collects and concentrates aerosols into fluid, which is passed through the fluidic channels of the microfluidics chip. The aerosol collector chip collects aerosols from air, water, and/or soil.

According to embodiments of the present invention, the SPP-based system and the Raman scattering-based system can be used simultaneously or individually separately to detect biological and/or chemical analytes. When used simultaneously, the reliability of bio-detection can be improved.

Embodiments of the present invention enable bio-threat detection systems capable of rapid detection and identification of airborne and/or waterborne biological and/or chemical analytes. Embodiments of the present invention can be used to detect a variety of biological and/or chemical analytes, including, for example, proteins, bacteria, toxins, allergens, HIV, the West Nile Virus, and the SARS-associated corona virus.

Embodiments of the present invention are amenable to the portability, packaging, and power requirements necessary for field deployment. Bio-threat detection systems according to the present invention can be particularly useful in places where pathogenic agents can spread through exposed populations at high rates, including, for example, hospitals, airports, and rail stations. Further, embodiments of the present invention can be used aboard means of propagation of biological and/or chemical analytes, including, for example, commercial aircrafts. Embodiments of the present invention can be used to enable an aircraft warning system.

Embodiments of to the present invention enable multi-element, highly parallel multi-media sensing (e.g., exhaled breath, air, water, soil), high energy efficiency, and compact designs.

Embodiments according to the present invention are suitable for highly parallel, multi-element analysis, in which a single fluidics channel etched in the elastomer layer includes an array of sample wells (e.g., 100×100 array of sample wells.

Multi-Modal Surface Plasmon Polariton (SPP)—Raman Scattering Bio-Detection

FIG. 1 illustrates an example of a combined SPP-based and Raman scattering-based bio-detection system 100 according to an embodiment of the present invention. Bio-detection system 100 includes a laser 102, a light source 104, a polarizer 106, a microfluidics chip 108, an analyzer 110, a first detector 112, and a second detector 114. In an embodiment, bio-detection system 100 further includes an aerosol collector chip (not shown in FIG. 1), which is coupled to microfluidics chip 108.

Microfluidics chip 108 includes a sensor of biological and chemical analytes (e.g., infectious viral particles, biowarfare agents, etc.) or biological and/or chemical analytes. Embodiments of microfluidics chip 108 will now be described with reference to FIGS. 2-4.

Figure 2:
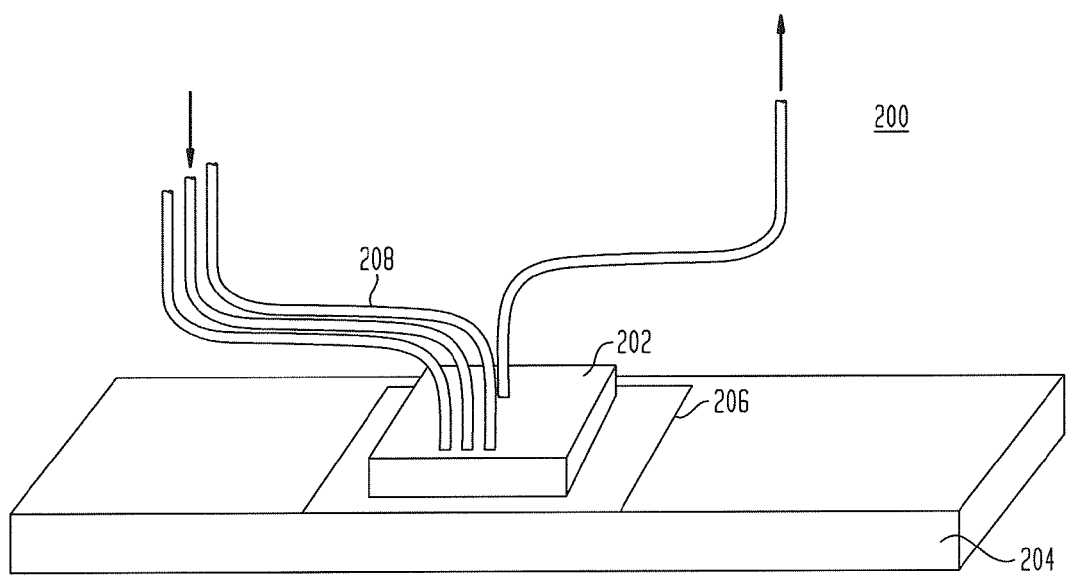
FIG. 2 illustrates an example microfluidics chip according to an embodiment of the present invention.

FIG. 2 illustrates an example microfluidics chip 200 according to an embodiment of the present invention. Microfluidics chip 200 includes an elastomer layer 202 having fluidic channels 208 constructed therein, coupled to a grating coupler. The grating coupler includes a glass substrate 204 coated with a gold layer 206. Accordingly, microfluidics chip 200 includes a gold-liquid interface (where fluidic channels 208 adjoin gold layer 206) and a glass-gold interface (where glass substrate 204 adjoins gold layer 206). In an embodiment, each fluidic channel may include an array of sample wells, thereby allowing multi-element, parallel analysis.

In an embodiment, elastomer layer 202 includes a clear polydimethylsiloxane (PDMS) layer.

Figure 3:
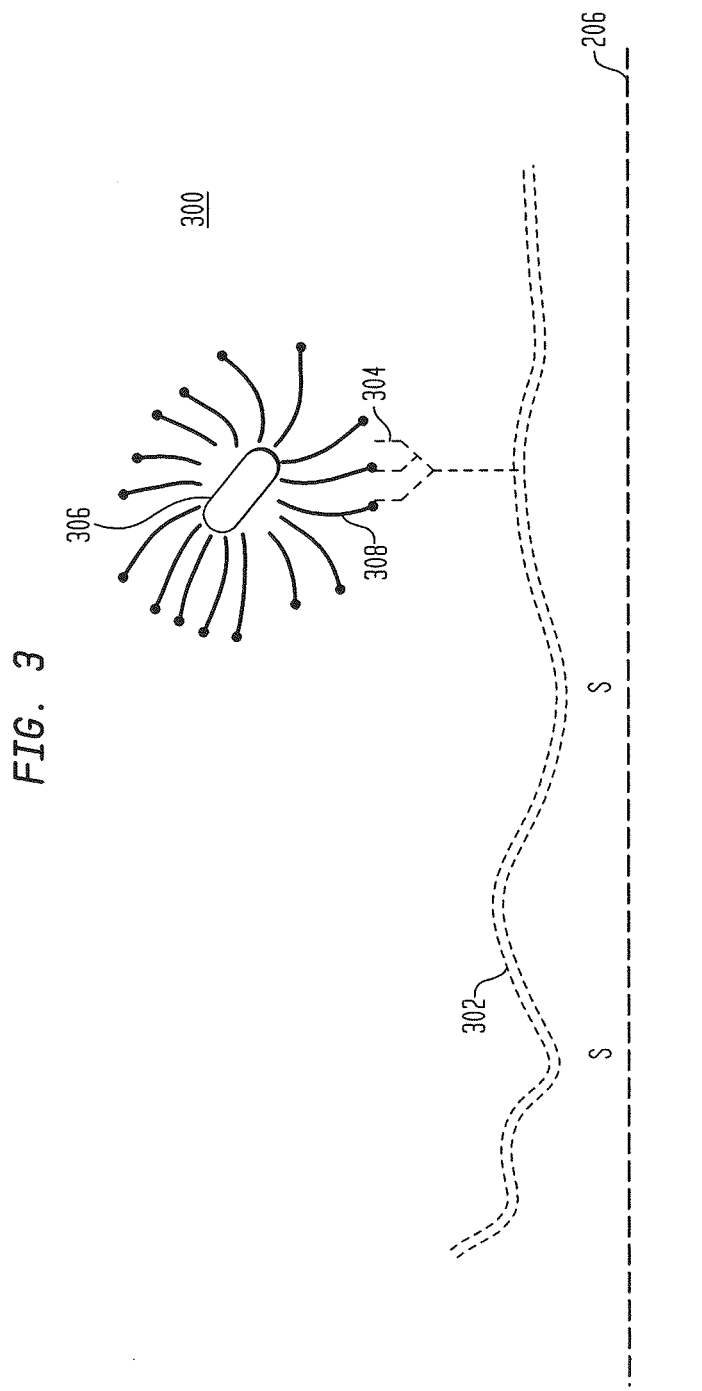
FIG. 3 illustrates the binding of biological and/or chemical analytes with bio-receptor molecules within a microfluidics chip according to an embodiment of the present invention.

Gold layer 206 is coated with bio-receptor molecules (e.g., oligosaccharides, peptides, antibodies, etc.). The bio-receptor molecules act as sensors of biological and/or chemical analytes by binding with biological and/or chemical analytes when present in a fluid passed through fluidic channels 208 over gold layer 206. In an embodiment, gold layer 206 is coated with different types of bio-receptor molecules with different concentrations per bio-receptor molecule. For example, gold layer 206 can be divided into a plurality of channels (each channel having a certain width and length), with each channel dedicated to a given bio-receptor molecule at a given concentration, where each bio-receptor molecule is known to bind with a corresponding biological and/or chemical analytes. This coupled with the elastomer layer having fluidics channels, each having an array of sample wells, allows for multi-element, highly parallel analysis. FIG. 3 illustrates an example 300 of the binding of biological and/or chemical analytes with bio-receptor molecules within a microfluidics chip according to the present invention. As shown in FIG. 3, a perforated gold layer 202 is coated with bio-receptor molecules 302. Related techniques useful for coating gold layer 202 with bio-receptor molecules can be found in U.S. Pat. No. 7,148,031 of common assignee, titled "Sequestering of glycoprotein molecules and oligosaccharide moieties in lipo-glycoprotein membranes and micelles." Bio-receptor molecules 302 can be, for example, glycoprotein molecules having complex carbohydrates covalently attached thereto. The complex carbohydrates attached to the glycoprotein project target sugars 304 into the medium. As such, when biological analytes 306 are present in the fluid passed over gold layer 208, target sugars 304 bind to proteins 308 (e.g., lectins) which are typically found on the surface of the biological analytes. Similarly, chemical analytes such as metals can be captured by carbohydrate receptors. Changes in characteristics within microfluidics chip 200 due to this binding are then detected, as will be further described below, to achieve bio-detection. According to embodiments of the present invention, this can be done by using the microfluidics chip within an SPP-based system, a Raman scattering-based system, or a combined SPP-based and Raman scattering-based system.

Figure 4:
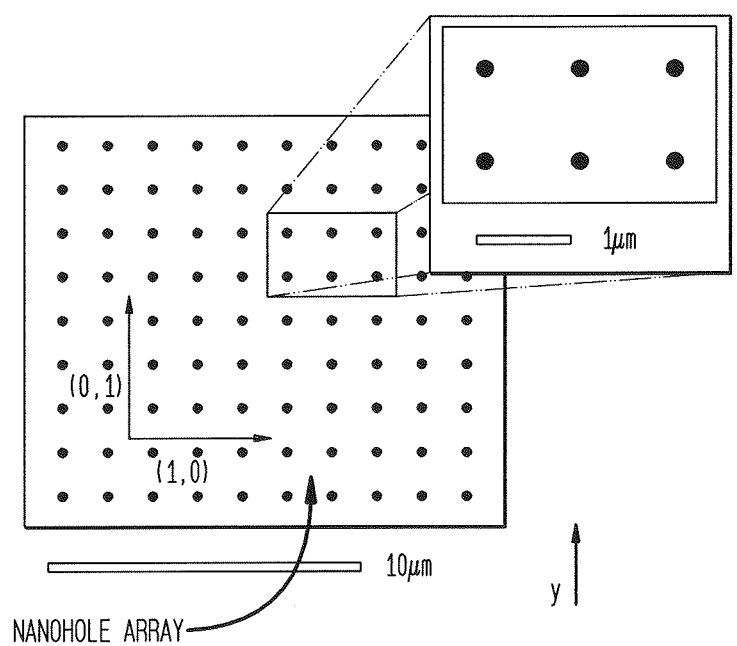
FIG. 4 illustrates an example gold nanohole array according to an embodiment of the present invention.

In an embodiment, gold layer 206 is etched to form a gold nanohole array. In an embodiment, the gold nanohole array includes a two-dimensional array of regularly-spaced nanoholes. FIG. 4 illustrates an example gold nanohole array 400 according to an embodiment of the present invention. As shown, the spacing between adjacent nanoholes of same row or same column (period of the array) can be on the order of 1 micron, for example. In an embodiment, a nanohole diameter is approximately 200 nm and thickness of gold is typically <200 nm.

Referring back to FIG. 1, laser 102 is a tunable laser. In an embodiment, laser 102 is a collimated tunable laser with 1 pm wavelength resolution (1520 nm-1570 nm, 6.9 dBm). In other embodiments, lasers with different wavelength characteristics can be used. As shown in FIG. 1, laser 102 generates a laser beam 116 that is directed at microfluidics chip 108. In an embodiment, laser beam 116 is directed at microfluidics chip 108 so as to illuminate a particular interface (e.g., gold-liquid or gold-glass) within microfluidics chip 108. In another embodiment, laser beam 116 has a wavelength and angle of incidence relative to microfluidics chip 108, configured to cause resonant excitation of surface plasmon polaritons that propagate along the gold-liquid interface within microfluidics chip 108. In an embodiment, the wavelength of laser beam 116 is configured according to a spacing between adjacent nanoholes within the nanohole gold array of microfluidics chip 108. In a further embodiment, laser beam 116 can also be used to cause resonant excitation of surface plasmon polaritons that propagate along the gold-glass interface within microfluidics chip 108.

Before reaching microfluidics chip 108, however, laser beam 116 is polarized by passing through polarizer 106 to generate a polarized laser beam 118. In an embodiment, polarized laser beam 118 is polarized according to a first polarization.

As described above, when polarized laser beam 118 illuminates microfluidics chip 108 at proper angle of incidence and wavelength, it causes resonant excitation of surface plasmon polaritons from several modes of the gold nanohole array within microfluidics chip 108. In particular, resonant photons are generated as a result of the interaction of polarized laser beam 118 with surface plasmon polaritons within microfluidics chip 108. The resonant photons have different polarizations than polarized laser beam 118. Accordingly, resultant laser beam 120 includes photons from polarized laser beam 118, polarized according to the first polarization, and photons from the resonant photons, having other polarizations.

Analyzer 110 forms an orthogonally-crossed polarizer-analyzer pair with polarizer 106. In other words, analyzer 110 filters out all light polarized according to the first polarization, generated by polarizer 106. As such, when resultant laser beam 120 is passed through analyzer 110, only resonant photons which result from the interaction between polarized laser beam 118 and surface plasmon polaritons pass through analyzer 110, generating filtered light 122.

An energy is associated with filtered light 122. The energy of filtered light 122 can be measured using an energy detector such as detector 112 in FIG. 1. Detector 112 may be a photodetector such as a photodiode, for example, or equivalent means for detecting and measuring illumination energy.

As would be understood by a person skilled in the art based on the teachings herein, the energy of filtered light 122 may change with changes in the process/setup that result in filtered light 122. For example, the energy of filtered light 122 may change with changes in the wavelength and/or the angle of incidence of laser beam 116. Further, changes of certain characteristics within microfluidics chip 108 (e.g., index of refraction at the gold-liquid interface) may also affect the energy of filtered light 122.

According to an embodiment of the present invention, components of bio-detection system 100 (e.g., laser 102, polarizer 106, and chip 108) are initially configured so as to cause resonant excitation of surface plasmon polaritons within microfluidics chip 108. This configuration, which may be conducted and verified at manufacture time of bio-detection system 100, may include generating an energy dispersion map (a 3-dimensional plot relating the energy of filtered light 122, the wavelength of laser beam 116, and the angle of incidence of laser beam 116 relative to chip 108) and selecting the coordinates within the dispersion map that result in a maximum energy of filtered light 122.

Subsequently, components of bio-detection system 100 are fixed according to this configuration. As such, any changes in the energy of filtered light 122 can only be attributed to changes of characteristics within microfluidics chip 108, or, in other words, to changes due to the binding of biological and/or chemical analytes with bio-receptor molecules within microfluidics chip 108.

According to an embodiment of the present invention, bio-detection system 100 is calibrated prior to use to ensure proper configuration. Subsequently, changes in the energy of filtered light 122 are monitored and measured to determine the presence of biological and/or chemical analytes within microfluidics chip 108. In an embodiment, the binding of biological and/or chemical analytes with bio-receptor molecules within microfluidics chip 108 causes local refractive index changes (due to positive shifts in the dielectric constant at the gold-liquid interface of microfluidics chip 108) within microfluidics chip 108. The local refractive changes, in turn, cause a shift in the wavelength/angle of incidence of laser beam 116 that result in the maximum energy of filtered light 122 (i.e., resonant wavelength/angle of incidence). In other words, the local refractive index changes cause changes in the measured energy of filtered light 122, when the wavelength and angle of incidence of laser beam 116 remain constant.

As described above, one performance criterion of bio-detection systems is the probability of false alarm. Accordingly, it is important to reduce factors that can result in false detection of biological and/or chemical analytes. In particular, it is important to reduce detection errors that result from variations in temperature, pressure, and/or flow. A mechanism for reducing the effects of temperature, pressure, and/or flow variations is described below. This mechanism is made available by virtue of the grating coupling used within the microfluidics chip, which allows for the generation of one or more SPP modes (e.g., a first SPP mode at the gold-liquid interface and a second SPP mode at the gold-glass interface of the microfluidics chip).

As described above, when laser beam 116 is directed at the gold-glass interface of microfluidics chip 108, it can cause (with proper configuration) resonant excitation of surface plasmon polaritons that propagate along the gold-glass interface. Surface plasmon polaritons that propagate along the gold-glass interface are invariant to refractive index changes that occur at the gold-liquid interface (due to the presence of biological and/or chemical analytes). Similarly, resonant photons that result from the interaction of light with the surface plasmon polaritons along the gold-glass interface (and the energy thereof) are invariant to refractive index changes at the gold-liquid interface (due to the presence of biological and/or chemical analytes). Accordingly, changes in the energy of these resonant photons can only be attributed to drifting conditions (e.g., temperature, pressure, and/or flow variations), not due to the presence of biological and/or chemical analytes.

Accordingly, an embodiment of the present invention further includes means for measuring the energy associated with resonant photons that result from the interaction of light with surface plasmon polaritons that propagate along the gold-glass interface; means for measuring changes in said energy; and means for compensating/calibrating measurements of the energy of filtered light 122 according to changes in the energy of resonant photons along the gold-glass interface.

As described above, bio-detection system 100 may further include an aerosol collector chip (not shown in FIG. 1), which can be coupled to microfluidics chip 108. In an embodiment, the aerosol collector chip is coupled to the fluidics channels of microfluidics chip 108. The aerosol collector chip collects and concentrates aerosols into fluid and passes the fluid through the fluidics channels of microfluidics channel 108. In an embodiment, the aerosol collector chip collects aerosols from exhaled breath, air, water, and/or soil.

In addition to the SPP-based system component of bio-detection system 100 described thus far, bio-detection system 100 further includes a Raman scattering-based system component. The Raman scattering-based component detects Raman-scattered photons, which result from changes in vibrational, rotational or electronic energy of the bio-receptor molecules of microfluidics chip 108 when they bind with biological and/or chemical analytes. The Raman scattering-based component of bio-detection system 100 will now be described.

Referring back to FIG. 1, bio-detection system 100 includes a light source 104 and a detector 114. In an embodiment, light source 104 can be combined with laser 102. Alternatively, light source 104 can be separate from laser 104.

As shown in FIG. 1, light source 104 generates a light beam 124 having a first wavelength, which illuminates microfluidics chip 108. In an embodiment, light beam 124 is directed at the gold-liquid interface of microfluidics chip 108.

Scattered light 126, which scatters from microfluidics chip 108 as a result of illumination by light beam 124, is received by detector 114. In an embodiment, detector 114 includes a spectrogram, which generates a wavelength spectrum of light 126 and detects photons within light 126 having wavelengths different than the first wavelength of incident light beam 124. These photons are known as Raman-scattered photons. As would be understood by a person skilled in the art, when light is scattered from a molecule, the majority of photons are elastically scattered (i.e., have the same energy, frequency, and wavelength as the incident light) and a very small fraction (approximately 1 in 100 millions photons) are inelastically scattered (i.e., have frequencies different from the frequency of the incident light).

The intensity of Raman-scattered photons varies with changes at the surface of the gold-liquid interface of microfluidics chip 108. In particular, the intensity of Raman-scattered photons varies with changes in vibrational, rotational or electronic energy of the bio-receptor molecules of microfluidics chip 108 as they bind with biological and/or chemical analytes. As such, by monitoring changes in the intensity/energy of Raman-scattered photons, the presence of biological and/or chemical analytes can be detected according to embodiments of the present invention.

According to embodiments of the present invention, Raman-scattering of photons is enhanced due to the nanohole array etched on the gold layer of microfluidics chip 108. This is known as hole-enhanced Raman scattering (HERS). Further, Raman-scattering of photons is enhanced due to the use of grating coupling within microfluidics chip 108. This is known as surface-enhanced Raman scattering (SERS). Enhanced Raman scattering is easier to detect and measure.

According to embodiments of the present invention, the SPP-based system component and the Raman scattering-based system component of bio-detection system 100 can be used simultaneously or individually separately. When used simultaneously, the reliability of bio-detection can be significantly improved.

In an embodiment, the SPP-based system component and the Raman scattering-based system component are substantially orthogonal to each other. Accordingly, neither system component affects the functionality/operation of the other system component. Alternatively, the SPP-based component and the Raman scattering-based component are not substantially orthogonal. Embodiments of the present invention thus may further include means for measuring the correlation between the SPP-based component and the Raman scattering-based, and means for compensating for the measured correlation within each system component.

As described above, embodiments of the present invention allow for the generation of one or more SPP modes within microfluidics chip 108. For example, a first SPP mode can be generated at the gold-liquid interface of the microfluidics chip and a second SPP mode can be generated at the gold-glass interface of the microfluidics chip. However, the ability to generate the first and/or second SPP modes depends on the ability to accurately direct a laser beam at the appropriate interface (gold-liquid or gold-glass) of microfluidics chip 108.

Figure 5:
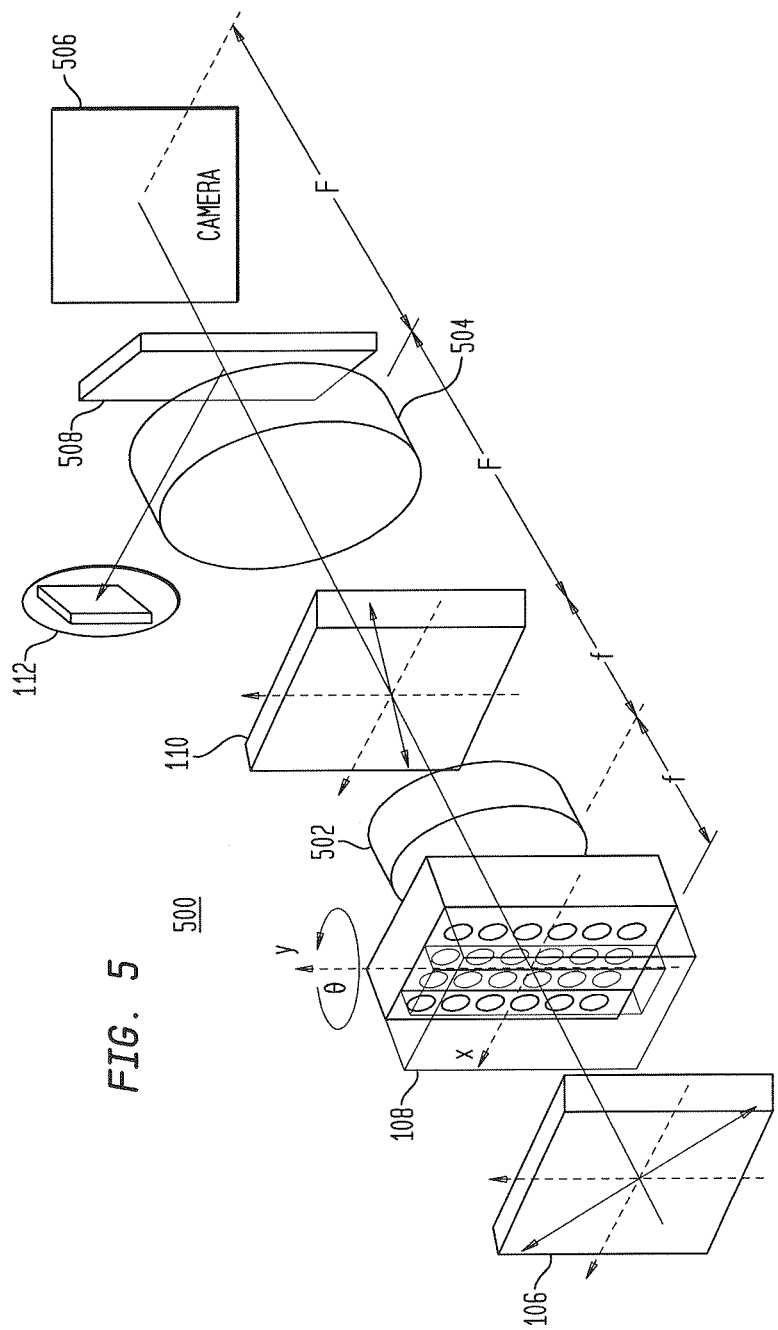
FIG. 5 is an example setup of the SPP-based component of a bio-detection system according to an embodiment of the present invention.

FIG. 5 is an example setup 500 of the SPP-based component of a bio-detection system according to the present invention. As shown, setup 500 uses a polarizer 106, a microfluidics chip 108, an analyzer 110, and a detector 112, as described above in FIG. 1. Setup 500 further includes a first lens 502, a second lens 504, a beam splitter 508, and a camera 506.

Lenses 502 and 504 focus the resonant photons that result from the laser illumination of microfluidics chip 108 towards beam splitter 508. As shown, beam splitter 508 splits the incident beam of resonant photons into two identical beams and directs one beam towards detector 112 and the other beam towards camera 506. This allows for simultaneous measurement of resonant energy using detector 112 and imaging of microfluidics chip 108 using camera 506. In an embodiment, camera 506 can be an InGaAs camera, which provides a zoomed-in view of microfluidics chip 108. The zoomed-in view of microfluidics facilitates the directing of the laser beam at the appropriate portion of microfluidics chip 108.

FIG. 10 is process flowchart 1000 of a method for bio-detection according to an embodiment of the present invention. The bio-detection method allows for SPP-based bio-detection, Raman scattering-based bio-detection, or combined SPP-based and Raman scattering-based bio-detection.

Process flowchart 1000 begins in step 1002, which includes directing light at a microfluidics chip. In an embodiment, the light includes a laser beam, and step 1002 further includes controlling the laser beam to generate a first surface plasmon polariton (SPP) mode along a gold-fluid interface of the microfluidics chip and/or a second SPP mode along a gold-glass interface of the microfluidics chip.

Subsequently, simultaneously, alternatively, or sequentially, process 1000 proceeds to steps 1004 and/or 1006.

Step 1004 includes detecting refractive index changes within the microfluidics chip, wherein the refractive index changes result when bio-receptor molecules within the microfluidics chip bind with biological and/or chemical analytes. In an embodiment, step 1004 further includes measuring a first energy associated with photons of the light that interact with surface plasmon polaritons that propagate along the gold-liquid interface; and measuring changes in the first energy, wherein changes in the first energy occur as a result of the refractive index changes within the microfluidics chip.

Step 1006 includes detecting Raman scattered photons that result from changes in vibrational, rotational, or electronic energy of the bio-receptor molecules when the bio-receptor molecules bind with biological and/or chemical analytes. In an embodiment, step 1006 further includes generating a wavelength spectrum of photons scattered as a result of the light being directed at the microfluidics chip, and detecting scattered photons having a wavelength different than a wavelength of said light.

After performing steps 1004 and/or 1006, process 1000 proceeds to step 1008, which includes combining detection results from steps 1004 and 1006 when both steps are performed, before generating a bio-detection result in step 1010. The bio-detection result indicates the presence of biological and/or chemical analytes or lack thereof.

Example Experimental Results

Example experimental results are described herein with reference to FIGS. 6-9. The example results are generated from a series of experiments involving an embodiment of the present invention used in SPP-based mode.

Figure 6:
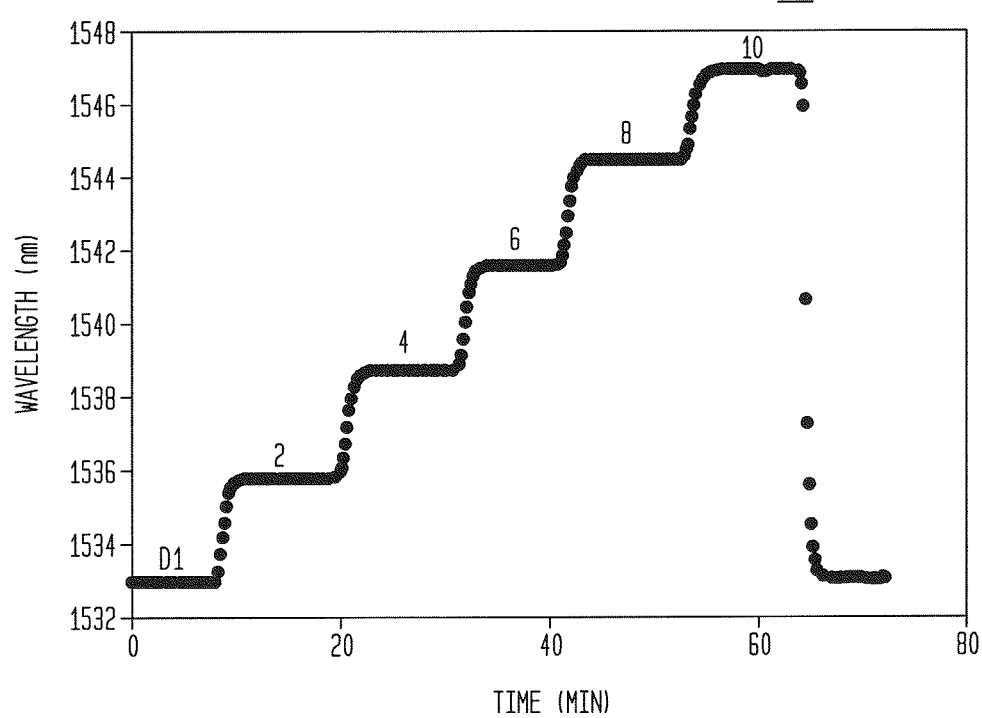
Figure 7:
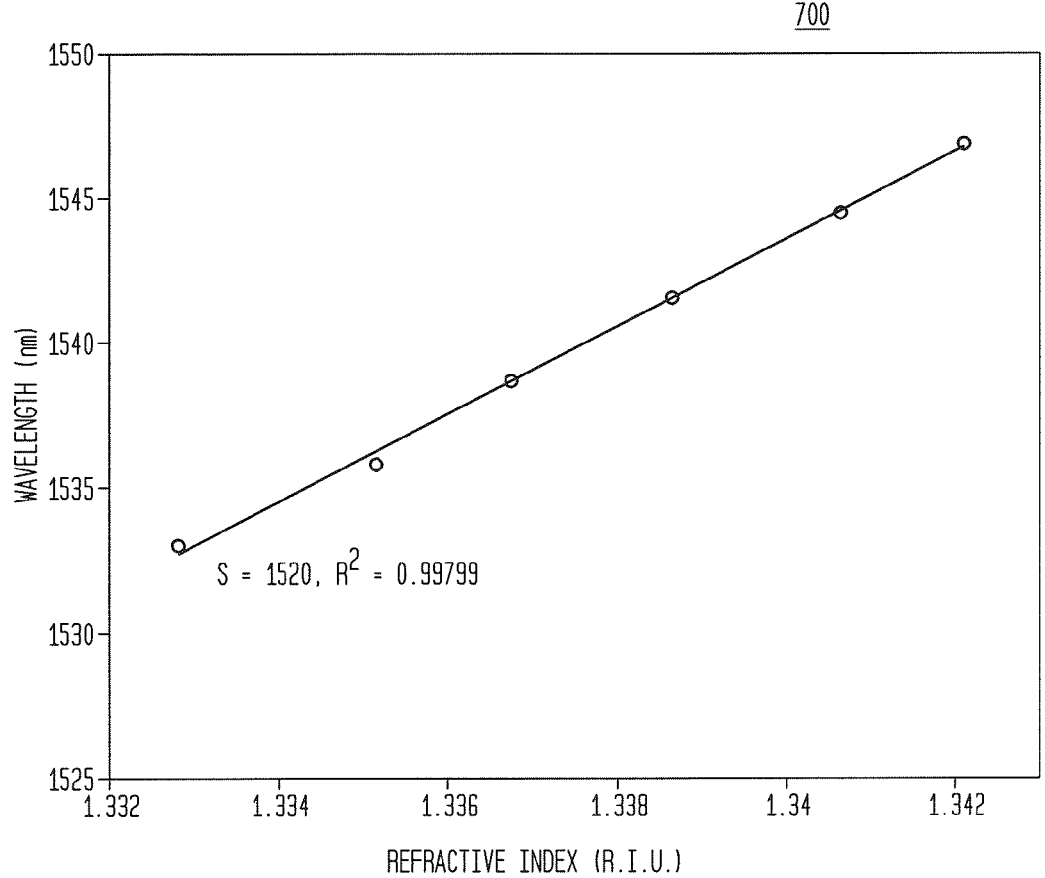

FIGS. 6 and 7 illustrate results from an experiment involving the detection of an ethylene glycol (EG) solution in de-ionized (DI) water. In performing the experiment, a series of ethylene glycol (EG) solutions ranging from 2% to 10% in weight were introduced into a microfluidics chip having a nanohole array with a period of 1.5 µm. The microfluidics chip includes a gold-liquid interface and a gold-glass interface, as described above. Measurements from one SPP mode from the gold-liquid interface are described below.

At t=0 minutes, the DI water at the interface was devoid of EG. Subsequently, a solution of 2% EG in DI water was added to the overlayer in incremental concentrations of 2% until a maximum of 10% EG was reached.

FIG. 6 is an example plot 600 that illustrates the shift in resonance peak wavelength as a function of time at the gold-liquid interface of the microfluidics chip, as EG concentrations are added. As shown, the resonant wavelength increases in nearly discrete steps with the addition of EG. At the end of the 10% EG test, DI water was introduced into the overlayer, which caused the SPP resonant wavelength to return to 1533 nm.

FIG. 7 is an example plot 700 that illustrates the shift in resonance peak wavelength as a function of the refractive index unit (RIU) at the gold-liquid interface of the microfluidics chip, also as a result of the added concentrations EG. As shown, the resonant peak wavelength varies directly proportionally with the RIU of the interface.

Figure 8:
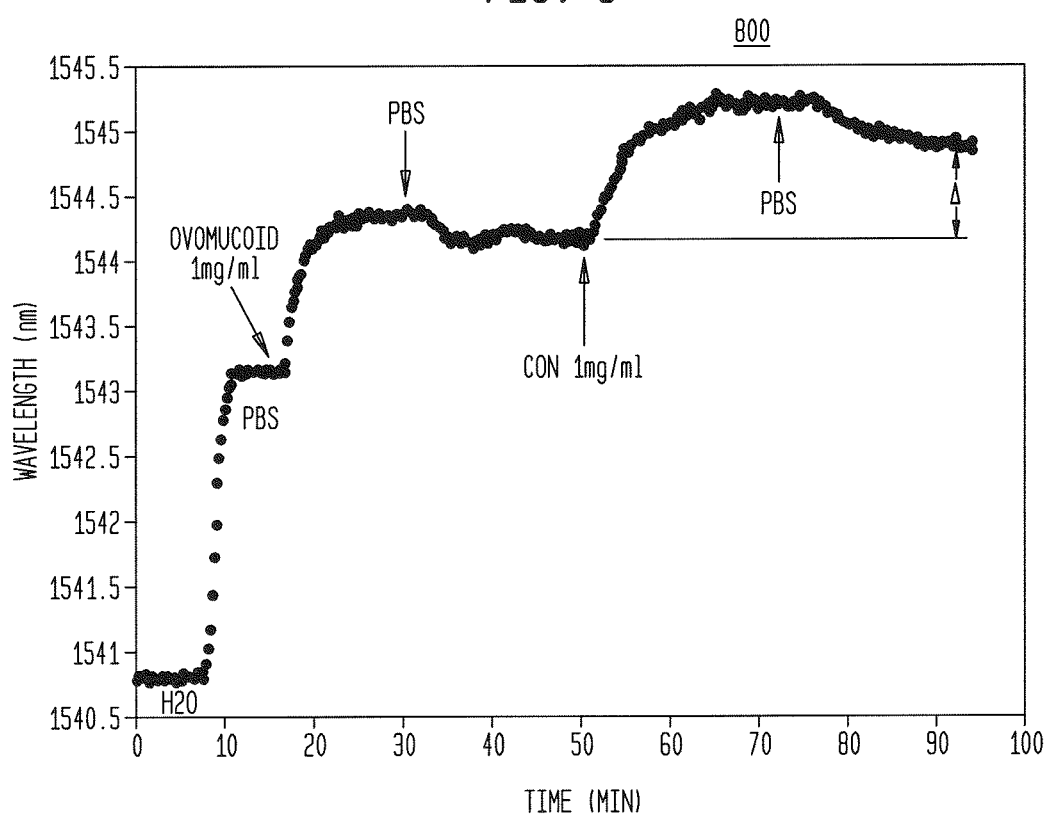

Protein-carbohydrate binding and protein-protein binding were also explored using the same SPP-based setup, as illustrated respectively in the example results of FIGS. 8 and 9.

FIG. 8 is an example plot 800 that illustrates the shift in resonance peak wavelength as a function of time at the gold-liquid interface of the microfluidics chip, as a result of protein-carbohydrate binding involving a protein, Concanavalin A (ConA), and ovomucoid molecules. At t=0 minutes, a water solution is used to wash the fluidic channels of the microfluidics chip. Subsequently, approximately 3 ml of sterile, neutral, PBS buffer solution is introduced, which causes an increase in resonant wavelength to approximately 1543 nm. When the resonant wavelength stabilized, approximately 3 ml of 1 mg/ml of ovomucoid was introduced at t=~18 minutes. The ovomucoid was allowed to adsorb to the gold layer of the microfluidics chip. An increase in resonant wavelength was observed to approximately 1544.5 nm. Then, a PBS solution was again introduced to wash away excess unbound ovomucoid. At t=~50 minutes, ~1 ml of 1 mg/ml of ConA was introduced. An increase in resonant wavelength was again observed as a result of binding between the ovomucoid and ConA. A PBS solution was again introduced at t=~70 minutes to wash away excess unbound ConA. At t=95 minutes, the resonant wavelength remained at ~1544.7 nm, which was 0.72 nm ($\Delta$) larger than pre-ConA resonant wavelength. This final shift, $\Delta$, was then used to calculate an estimate detection limit for ConA, by dividing it by the repeatability of the laser user (in this experiment, 0.8 nm/0.1 nm=8). Therefore, an estimated detection limit for ConA was found to be approximately 125 µg/ml (or ~4.6 µM).

FIG. 9 is an example plot 900 that illustrates the shift in resonance peak wavelength as a function of time at the gold-liquid interface of the microfluidics chip, as a result of protein-protein binding involving monoclonal anti-bovine serum albumin (anti-BSA) and BSA. Initially, fluid at the gold-liquid interface is displaced with an SDS solution, followed by DI water injection, and then ~3 ml of PBS. An increase in resonant wavelength is observed in response to PBS. When the resonant wavelength stabilized at t=~80 minutes, ~3 ml of 1 mg/ml of BSA was introduced. The BSA was allowed to adsorb to the gold layer of the microfluidics chip. Then, PBS was again added to wash away excess unbound BSA. BSA was then again allowed to adsorb to the gold layer for a total of 20 additional hours. A systematic instrumentation drift was observed over the extended deposition period as shown in FIG. 9. Thereafter, PBS was introduced to wash away any remaining unbound BSA. Then, ~1 ml of purified monoclonal anti-BSA was introduced at ~33 µg/ml (~232 nM), followed by the addition of PBS to wash away unbound anti-BSA. A shift in resonant wavelength was observed due to the binding of anti-BSA and BSA. The resonant wavelength then remained at 1536.4 nm, which was 0.72 nm ($\Delta$) larger than pre-anti-BSA resonant wavelength. An estimated detection limit was then calculated, as described above, and was found to be approximately 3.85 µg/ml (or ~27.5 nM).

CONCLUSION

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A method for bio-detection using a microfluidics chip having a liquid-metal (LM) interface and a substrate-metal (SM) interface, comprising:
    directing light at said microfluidics chip;
    measuring a first energy associated with photons of said light that interact with a first surface plasmon polariton (SPP) mode of said LM interface;
    measuring changes in said first energy;
    measuring a second energy associated with photons of said light that interact with a second SPP mode of said SM interface;
    measuring changes in said second energy;
    calibrating said changes in said first energy according to said changes in said second energy; and
    detecting, using said calibrated changes in said first energy, refractive index changes within said microfluidics chip, wherein said refractive index changes result from bio-receptor molecules within said microfluidics chip binding with analytes,
    wherein said microfluidics chip comprises a nanohole array.

2. The method of claim 1, wherein said light includes a laser beam.

3. The method of claim 2, further comprising:
controlling said laser beam to generate said SPP mode along said LM interface of said microfluidics chip and said second SPP mode along said SM interface of said microfluidics chip.

4. The method of claim 1, wherein said changes in said first energy occur as a result of said refractive index changes within said microfluidics chip.

5. The method of claim 1, wherein said first SPP mode varies when binding occurs between said bio-receptor molecules and said analytes, and wherein said second SPP mode is invariant to said binding.

6. The method of claim 1, further comprising:
detecting Raman scattered photons that result from changes in vibrational, rotational, or electronic energy of said bio-receptor molecules when said bio-receptor molecules bind with said analytes.

7. The method of claim 6, wherein said step of detecting Raman scattered photons comprises:
generating a wavelength spectrum of photons scattered as a result of said light being directed at said microfluidics chip; and
detecting scattered photons having wavelengths different than a wavelength of said light.

8. The method of claim 6, further comprising:
combining detection results from said detecting steps to generate a bio-detection result, wherein said bio-detection result indicates a presence of said analytes or a lack thereof.

9. The method of claim 1, wherein said bio-receptor molecules include one or more of complex carbohydrates, lectins, peptides, or anti-bodies.

10. The method of claim 9, wherein said bio-receptor molecules are applied simultaneously to different areas of a gold layer of said microfluidics chip, and wherein each of said bio-receptor molecules is dedicated to detecting a respective analyte, thereby allowing multi-element bio-detection.

11. A method for bio-detection using a microfluidics chip having a liquid-metal (LM) interface and a substrate-metal (SM) interface, comprising:
measuring a first energy associated with photons of light that interact with a first surface plasmon polariton (SPP) mode of said LM interface of said microfluidics chip;
measuring changes in said first energy;
measuring a second energy associated with photons of light that interact with a second SPP mode of said SM interface of said microfluidics chip;
measuring changes in said second energy;
calibrating said changes in said first energy according to said changes in said second energy; and
detecting, using said calibrated changes in said first energy, refractive index changes within said microfluidics chip, wherein said refractive index changes result from bio-receptor molecules within said microfluidics chip binding with analytes,
wherein said microfluidics chip comprises a nanohole array.

12. The method of claim 1, wherein said changes in said second energy are due to variations in temperature, pressure, and/or flow.

13. The method of claim 12, wherein said calibrated changes in said first energy are substantially free of changes due to variations in temperature, pressure, and/or flow.

14. The method of claim 11, further comprising:
detecting Raman scattered photons that result from changes in vibrational, rotational, or electronic energy of said bio-receptor molecules when said bio-receptor molecules bind with said analytes.

15. The method of claim 14, further comprising:
combining detection results from said detecting steps to generate a bio-detection result, wherein said bio-detection result indicates a presence of said analytes or a lack thereof.

16. The method of claim 11, wherein said first SPP mode varies when binding occurs between said bio-receptor molecules and said analytes, and wherein said second SPP mode is invariant to said binding.

17. The method of claim 11, further comprising:
directing light at said LM interface of said microfluidics chip to generate said first SPP mode; and
directing light at said SM interface of said microfluidics chip to generate said second SPP mode.

18. The method of claim 11, wherein said changes in said second energy are due to variations in temperature, pressure, and/or flow.

19. The method of claim 18, wherein said calibrated changes in said first energy are substantially free of changes due to variations in temperature, pressure, and/or flow.

* * * * *